United States Patent [19]

Kuhla et al.

[11] 3,961,065

[45] June 1, 1976

[54] BENZENESULFONYLUREA DERIVATIVES

[75] Inventors: Donald E. Kuhla, Gales Ferry; Reinhard Sarges, Mystic, both of Conn.

[73] Assignee: Pfizer Inc., New York, N.Y.

[22] Filed: Jan. 30, 1975

[21] Appl. No.: 545,741

Related U.S. Application Data

[62] Division of Ser. No. 357,466, May 4, 1973, Pat. No. 3,879,403.

[52] U.S. Cl. ............................................. 424/266
[51] Int. Cl.² ........................................ A61K 31/455
[58] Field of Search ................................... 424/266

[56] References Cited
FOREIGN PATENTS OR APPLICATIONS 667,769  2/1966  Belgium ..................... 260/294.8 H

*Primary Examiner*—Jerome D. Goldberg
*Attorney, Agent, or Firm*—Connolly and Hutz

[57] ABSTRACT

Certain novel benzenesulfonylurea compounds derived from a nitrogen-containing carboxylic acid have been prepared by reacting an appropriate sulfonamide with an organic isocyanate or a tri-substituted urea equivalent thereof. The sulfonylureas so obtained are useful in therapy as oral hypoglycemic agents. Typical members include those compounds derived from 2-methoxy-nicotinic acid, of which 1-cyclohexyl-3-{4-[2-(5-bromo-2-methoxynicotinamido)ethyl]benzenesulfonyl}urea is a most preferred embodiment.

14 Claims, No Drawings

BENZENESULFONYLUREA DERIVATIVES

CROSS REFERENCE TO RELATED APPLICATION

This application is a division of application Ser. No. 357,466 filed May 4, 1973 now U.S. Pat. No. 3,879,403.

BACKGROUND OF THE INVENTION

This invention relates to new and useful sulfonylurea derivatives, which are effective in reducing blood sugar levels to a remarkably high degree. More particularly, it is concerned with certain novel benzenesulfonylureas and their base salts with pharmacologically acceptable cations, which are useful in therapy as oral hypoglycemic agents for the treatment of diabetes.

In the past, various attempts have been made by numerous investigators in the field of organic medicinal chemistry to obtain new and better oral hypoglycemic agents. For the most part, these efforts have principally involved the synthesis and testing of various new and heretofore unavailable organic compounds, particularly in the area of the sulfonylureas and the various biguanidine derivatives. However, in the search for still newer and more improved oral hypoglycemic agents, far less is known about the activity of various substituted carboxamidobenzene sulfonylureas such as those which are derived from certain heterocyclic monocarboxylic acids. For instance, Belgian Patent No. 667,769 discloses several acylamino-derived benzenesulfonylureas which contain a pyridine ring and are reported to be active as hypoglycemic agents, but none of these aforementioned compounds presently process any known clinical advantages over that of either chlorpropamide or tolbutamide when used in the treatment of diabetes.

SUMMARY OF THE INVENTION

In accordance with the present invention, it has now been rather surprisingly found that certain novel benzenesulfonylureas derived from a nitrogen-containing monocarboxylic acid are extremely useful when employed as hypoglycemic agents for the treatment of diabetic subjects with a single oral dose per day. The novel sulfonylurea compounds of this invention are all selected from the group consisting of benzenesulfonylureas of the formula:

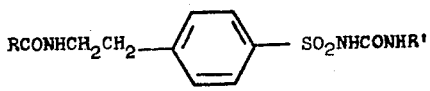

and the base salts thereof with pharmacologically acceptable cations, wherein R is 2-methoxy-3-pyridyl, 5-chloro-2-methoxy-3-pyridyl or 5-bromo-2-methoxy-3-pyridyl, and R' is bicyclo[2.2.1]-hept-5-en-2-yl-endo-methyl, cyclohexyl or 4-chlorocyclohexyl. Typical member compounds specifically embraced by this invention include 1-(bicyclo[2.2.1]hept-5-en-2-yl-endo-methyl)-3-{4-[2-(2-methoxynicotinamido)ethyl]benzenesulfonyl}urea, 1-cyclohexyl-3-{4-[2-(2-methoxynicotinamido)ethyl]benzenesulfonyl}urea, 1-(bicyclo[2.2.1]hept-5-en-2-yl-endo-methyl)-3-{4-[2-(5-chloro-2-methoxynicotinamido)ethyl]benzenesulfonyl}urea, 1-cyclohexyl-3-{4-[2-(5-chloro-2-methoxynicotinamido)ethyl]benzenesulfonyl}-urea, 1-(4-chlorocyclohexyl)-3-{4-[2-(5-chloro-2-methoxynicotinamido)ethyl]benzenesulfonyl}urea, 1-(bicyclo[2.2.1]hept-5-en-2-yl-endo-methyl)-3-{4-[2-(5-bromo-2-methoxynicotinamido)ethyl]-benzenesulfonyl}urea and 1-cyclohexyl-3-{4-[2-(5-bromo-2-methoxynicotinamido)ethyl]benzenesulfonyl}urea and their corresponding sodium salts. These particular compounds are all highly potent as regards their hypoglycemic activity and therefore, are extremely useful in lowering blood sugar levels when given by the oral route of administration. Moreover, these novel agents all possess a long plasma half-life and hence, need only be given but once a day when used in treating diabetic subjects for the present purposes at hand.

DETAILED DESCRIPTION OF THE INVENTION

In accordance with the process employed for preparing the novel compounds of this invention, an appropriately substituted sulfonamide compound of the formula:

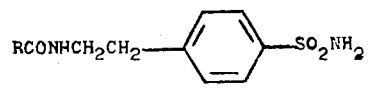

is reacted with an organic isocyanate reagent of the formula R'NCO wherein R' corresponds to the previously defined 1-substituent on the urea moiety of the desired final product. In this way, the corresponding benzenesulfonylurea compound is formed where R is defined as previously indicated. This particular reaction is normally conducted in a basic solvent medium, most desirably employing an aprotic organic solvent such as tetrahydrofuran, dimethylsulfoxide or dimethylformamide and preferably using a slight excess in moles of a base like triethylamine or sodium hydride (in mineral oil), which may then be admixed with the organic solvent. Many of the aforesaid isocyanate reagents (R'NCO) are either known compounds or else they can easily be prepared, using methods well-known to those skilled in the art, starting from readily available materials. In practice, it is usually preferable to employ at least about a molar equivalent of the isocyanate reagent in the aforesaid reaction of the present invention, with best results often being achieved by using a slight excess of same. Although any temperatures below that of reflux may be used in order to effect the reaction, it is normally found most convenient in practice to employ elevated temperatures so as to shorten the required reaction time, which may range anywhere from several minutes up to about 24 hours depending, of course, upon the particular benzenesulfonylurea actually being prepared. Upon completion of the reaction, the product is easily recovered from the spent reaction mixture in a convention manner, e.g., by pouring the mixture into an excess of ice-water containing a slight excess of acid, such as hydrochloric acid, whereby the desired benzenesulfonylurea readily precipitates from solution and is subsequently collected by such means as suction filtration and the like.

Another method for preparing the novel compounds of this invention involves reacting the benzenesulfonamide in the form of an alkali metal or alkaline-earth metal salt (either employed as such or else formed in situ) with an appropriate 1,1,3-tri-substituted urea of the formula (R")₂NCONHR', wherein R" is an aryl group such as phenyl, p-chlorophenyl, p-bromophenyl, p-nitrophenyl, p-acetylaminophenyl, p-tolyl, p-anisyl, α-naphthyl, β-naphthyl and the like. This reaction is preferably carried out in the presence of an inert polar organic solvent medium. Typical organic solvents for use in this connection include the N,N-dialkyl lower alkanoamides like dimethylformamide, dimethylacetamide, diethylformamide and diethylacetamide, as well as lower dialkyl sulfoxides such as dimethyl sulfoxide, diethyl sulfoxide and di-n-propyl sulfoxide, etc. It is desirable that the aforesaid solvent for this reaction be present in sufficient amount to dissolve each of the previously mentioned starting materials. In general, the reaction is conducted at a temperature that is in the range of from about 20°C. up to about 150°C. for a period of about ½ to about 10 hours. The relative amounts of reagents employed are such that the molar ratio of said benzenesulfonamide to the 1,1-diaryl-3-(monosubstituted)urea is most desirably in the range of from about 1:1 to about 1:2, respectively. Recovery of the desired product from the reaction mixture is then achieved by first diluting the reaction solution with water and thereafter adjusting if necessary the pH of the resulting solution to a value of at least about 8.0, followed by thorough extraction of the basic aqueous solution with any water-immiscible solvent in order to remove the diarylamine byproduct of formula $(R'\lambda')_2NH$ as well as minor amounts of unreacted or excess starting material that might still possibly be present. Isolation of the desired benzenesulfonylurea from the basic aqueous layer is then finally accomplished by adding a sufficient amount of dilute aqueous acid to the aforesaid basic solution to cause precipitation of the desired sulfonylurea therefrom.

The two major type starting materials required for this reaction, viz., the benzenesulfonamides and the 1,1-diaryl-3-(monosubstituted)ureas, are both readily prepared by those skilled in the art in accordance with conventional methods of organic chemistry. For instance, the benzenesulfonamides which are novel compounds and are also used as starting materials in the previously described isocyanate method, are suitably obtained by using classical methods of organic synthesis starting from the known 4-(2-aminoethyl)benzenesulfonamide and proceeding in accordance with the procedure described in some detail in the experimental section of this specification (e.g., see Preparations A–C in this regard). The 1,1-diaryl-3-(monosubstituted)ureas, on the other hand, are all readily prepared from common organic reagents by employing standard procedures well-known in the art. For example, the desired 1,1,3-trisubstituted urea may simply be obtained by treating the corresponding disubstituted carbamyl chloride of formula $(R'')_2NCOCl$ with the appropriate amine of formula $R'NH_2$ in accordance with the general reaction procedure described by J.F.L. Reudler in *Recueil des Travaux des Pays-Bas.*, Vol. 33, p. 64 (1914).

The chemical bases which are used as reagents in this invention to prepare the aforementioned pharmaceutically acceptable base salts are those which form non-toxic salts with the herein described acidic benzenesulfonylureas, such as 1-cyclohexyl-3-{4-[2-(5-bromo-2-methoxynicotinamido)ethyl]benzenesulfonyl}-urea, for example. These particular non-toxic base salts are of such a nature that their cations are deemed to be essentially non-toxic in character over the wide range of dosage administered. Examples of such cations include those of sodium, potassium, calcium and magnesium, etc. These salts can easily be prepared by simply treating the aforementioned benzenesulfonylureas with an aqueous solution of the desired pharmacologically acceptable base, i.e., those oxides, hydroxides, or carbonates which contain pharmacologically acceptable cations, and then evaporating the resulting solution to dryness while preferably being placed under reduced pressure. Alternatively, they may also be prepared by mixing lower alcoholic solutions of the said acidic compounds and the desired alkali metal alkoxide together, and then evaporating the resulting aforesaid solution in the same manner as before. In either case, stoichiometric amounts of reagents must be employed in order to ensure completeness of reaction and consequent maximum production of yields with respect to the desired salt product.

As previously indicated, the benzenesulfonylurea compounds of this invention are all readily adapted to therapeutic use as oral hypoglycemic agents, in view of their ability to lower the blood sugar levels of diabetic and non-diabetic subjects to a statistically significant degree. For instance, 1-cyclohexyl-3-{4-[2-(5-bromo-2-methoxynicotinamido)ethyl]benzenesulfonyl}urea (as the sodium salt), a typical and preferred agent of the present invention, has been found to consistently lower blood sugar levels in the normal fasted rat to a statistically significant degree when given by the oral or the intraperitoneal route of administration at dose levels ranging in either case from 0.1 mg./kg. to 5.0 mg./kg., respectively, without showing any substantial signs of toxic side effects. The other compounds of this invention also cause similar results. Furthermore, all the herein described compounds of this invention can be administered orally, for the present purposes at hand, without causing any significant untoward pharmacological side reactions to occur in the subject to whom they are so administered at dosage levels ranging from about 0.05 mg. to about 1.0 mg. per kg. of body weight per day, although variations will necessarily occur depending upon the condition and individual response of the subject being treated and the particular type of oral formulation chosen.

In connection with the use of the benzenesulfonylurea compounds of this invention for the treatment of diabetic subjects, it is to be noted that they may be administered either alone or in combination with pharmaceutically acceptable carriers and that such administration can be carried out in both single and multiple dosages. More particularly, the novel compounds of the invention can be administered in a wide variety of different dosage forms, i.e., they may be combined with various pharmaceutically-acceptable inert carriers in the form of tablets, capsules, lozenges, troches, hard candies, powders, aqueous suspension, elixirs, syrups and the like. Such carriers include solid diluents or fillers, sterile aqueous media and various non-toxic organic solvents, etc. Moreover, such oral pharmaceutical compositions can be suitably sweetened and/or flavored by means of various agents of the type commonly employed for just such a purpose. In general, the therapeutically-effective compounds of this invention, are present in such dosage forms at concentration levels ranging from about 0.5% to about 90% by weight of the total composition, i.e., in amounts which are sufficient to provide the desired unit dosage.

For purposes of oral administration, tablets containing various excipients such as sodium citrate, calcium carbonate and dicalcium phosphate may be employed along with various disintegrants such as starch and preferably potato or tapioca starch, alginic acid and certain complex silicates, together with binding agents such as polyvinylpyrrolidone, gelatin and acacia. Additionally, lubricating agents such as magnesium stearate, sodium lauryl sulfate and talc are often very useful for tabletting purposes. Solid compositions of a similar type may also be employed as fillers in soft and hard-filled gelatin capsules; preferred materials in this connection would also include the high molecular weight polyethylene glycols. When aqueous suspensions and-/or elixirs are desired for oral administration, the essential active ingredient therein may be combined with various sweetening or flavoring agents, coloring matter or dyes and, if so desired, emulsifying and/or suspending agents as well, together with such diluents as water, ethanol, propylene glycol, glycerin and various like combinations thereof.

The activity of the compounds of the present invention, as hypoglycemic agents, is determined by their ability to lower blood sugar levels in the normal fasted rat when tested therein for such purposes according to the procedure described by W. S. Hoffman, as reported in the *Journal of Biological Chemistry*, Vol. 120, p. 51 (1937). The latter method measures directly the amount of glucose in the blood at any given time and from this, the maximum percent decrease in blood sugar can be readily calculated and reported as hypoglycemic activity per se. In this way, the present benzenesulfonylurea compounds are shown to markedly reduced the blood sugar levels of non-anesthetized rate when administered to them at dose levels as low as 0.1 mg./kg.

PREPARATION A

A stirred suspension consisting of 57 g. (0.362 mole) of 2-chloronicotinic acid [G. M. Badger et al., *Australian Journal of Chemistry*, Vol. 18, p. 1267 (1965)] in 800 ml. of methanol was treated portion-wise with 43 g. (0.797 mole) of sodium methoxide. The resulting turbid solution was then heated in an autoclave at 110°C. for a period of 11 hours. The reaction mixture obtained in this manner was then evaporated to near dryness (while under reduced pressure) and the residue was subsequently dissolved in 2000 ml. of water, filtered and the resulting filtrate thereafter acidified with 1000 ml. of glacial acetic acid. The acidified filtrate was then concentrated in vacuo to a volume of ca. 800 ml., cooled in an ice bath for a period of approximately 1 hour and the resulting crystalline crop (i.e., the precipitate) thereafter collected by means of suction filtration. After air-drying to constant weight, there were obtained 33.3 g. (60%) of the final product melting at 143°–146°C. Crystallization of the latter material from 150 ml. of acetonitrile then gave 27.6 g. (60%) of pure 2-methoxynicotinic acid, m.p. 144°–146°C. [literature m.p. 144°–146°C., according to *Chemical Abstracts*, Vol. 68, p. 12876 (1968)].

To a suspension of 256 g. (1.675 mole) of 2-methoxynicotinic acid in 5.0 liters of methylene chloride, there were added 1000 ml. of thionyl chloride in one portion and the resulting reaction mixture was then heated on a steam bath to reflux temperature. After a period of 2 hours at the reflux point, the clear solution was cooled and then concentrated in vacuo at room temperature to afford a residual oil. The excess thionyl chloride present was next removed by adding 500 ml. of benzene and subsequently evaporating the mixture to dryness, while under reduced pressure. This particular purification step was repeated twice and there was ultimately obtained 288 g. of pure 2-methoxynicotinoyl chloride as the residue, which solidified on standing and was used as such in the next reaction step. The yield of product was nearly quantitative.

A solution consisting of 0.765 mg. (0.005 mole) of 2-methoxynicotinoyl chloride dissolved in 15 ml. of chloroform and a solution of 1.24 g. (0.001 mole) of sodium carbonate in 15 ml. of water were added simultaneously in a dropwise manner to 1.18 g. (0.005 mole) of 4-(2-aminoethyl)benzenesulfonamide hydrochloride [E. Miller et al., *Journal of the American Chemical Society*, Vol. 62, p. 2099 (1940)] dissolved in 15 ml. of water, which also contained 1.24 g. (0.01 mole) of sodium carbonate. Vigorous agitation was maintained throughout the addition step, after which the reaction mixture was then further stirred at room temperature (~25°C.) for a period of 1.5 hours. At this point, the precipitated solids which formed were immediately recovered by means of suction filtration, air-dried to constant weight and thereafter recrystallized from acetonitrile to give 1.04 g. (62%) of pure 4-[2-(2-methoxynicotinamido)ethyl]benzenesulfonamide. m.p. 176°–177°C.

Anal. Calcd. for $C_{15}H_{17}N_3O_4S$: C, 53.73; H, 5.11; N, 12.53. Found: C, 53.32; H, 5.05; H, 12.40.

PREPARATION B

A suspension of 10 g. (0.065 mole) of 2-methoxynicotinic acid in 750 ml. of water was treated with chlorine gas by bubbling a molar excess of same into the aforesaid stirred aqueous mixture, while maintaining the latter at room temperature (~25°C.) throughout the course of the entire addition step. Upon completion of the addition (this step required approximately 30 minutes), the precipitated solids which resulted were removed by means of filtration and subsequently air dried to constant weight to afford 10.2 g. (84%) of pure 5-chloro-2-methoxynicotinic acid, m.p. 149°–150°C.

Anal. Calcd. for $C_7H_6ClNO_3$: C, 44.84; H, 3.22; N, 7.40. Found: C, 44.99; H, 3.33; N, 7.56.

To a suspension of 3.76 g. (0.02 mole) of 5-chloro-2-methoxynicotinic acid in 100 ml. of carbon tetrachloride, there were added 100 ml. of thionyl chloride in one portion and the resulting mixture was then refluxed on a steam bath for a period of 90 minutes. Upon completion of this step, the clear solution so obtained was cooled and then concentrated in vacuo at room temperature to afford a residual oil. The excess thionyl chloride present was next removed in the same manner as described in Preparation A for the production of 2-methoxynicotinoyl chloride, except that only 100 ml. of benzene was employed this time (i.e., during each purification step). The yield of pure 5-chloro-2-methoxynicotinoyl chloride, obtained as the residual product, was quantitative in this particular instance.

A solution consisting of 4.74 g. (0.02 mole) of 5-chloro-2-methoxynicotinoyl chloride dissolved in 75 ml. of chloroform and a solution of 5.1 g. (0.048 mole) of sodium carbonate in 45 ml. of water were added simultaneously in a dropwise manner to 4.74 g. (0.02 mole) of 4-(2-aminoethyl)benzenesulfonamide hydrochloride dissolved in 30 ml. of water, which also contained 3.4 g. (0.032 mole) of sodium carbonate. Vigorous agitation was maintained throughout the course of the addition, after which the reaction mixture was then further stirred at room temperature for a period of 30 minutes. At this point, the precipitated solids which formed were immediately recovered by means of suction filtration, air-dried to constant weight and thereafter recrystallized from acetonitrile-methanol to afford 5.43 g. (73%) of pure 4-[5-chloro-2-methoxynicotinamido)ethyl]benzenesulfonamide, m.p. 210°–211°C.

Anal. Calcd. for $C_{15}H_{16}Cl_3N_3O_4S$: C, 48.71; H, 4.36; N, 11.36. Found: C, 48.85; H, 4.41; N, 11.51.

PREPARATION C

A suspension of 15.3 g. (0.10 mole) of 2-methoxynicotinic acid in 500 ml. of water was treated with 17.6 g. (0.11 mole) of liquid bromine, and the resulting mixture was heated to 45°–50°C. for a period of 70 minutes. On cooling to 0°C., there was obtained a crystalline precipitate which was subsequently collected by means of suction filtration and air-dried to constant weight. Recrystallization of the latter material from ethyl acetate/n-hexane then gave 15.5 g. (67%) of pure 5-bromo-2-methoxynicotinic acid, m.p. 158.5°–160°C.

Anal. Calcd. for $C_7H_6BrNO_3$: C, 36.24; H, 2.61; N, 6.04. Found: C, 36.39; H, 2.75; N, 5.85.

To a suspension of 15.4 g. (0.067 mole) of 5-bromo-2-methoxynicotinic acid in 200 ml. of carbon tetrachloride, there were added 200 ml. of thionyl chloride in one portion and the resulting mixture was thereafter treated in exactly the same way as that previously described in Preparation B for the production of the related 5-chloro compound. In this particular case, the corresponding final product actually obtained was 5-bromo-2-methoxynicotinoyl chloride and the yield of same was nearly quantitative.

A solution consisting of 16.7 g. (0.067 mole) of 5-bromo-2-methoxynicotinoyl chloride dissolved in 200 ml. of chloroform and a solution of 14.2 g. (0.134 mole) of sodium carbonate in 100 ml. of water were added simultaneously in a dropwise manner to 15.8 g. (0.067 mole) of 4-(2-aminoethyl)benzenesulfonamide dissolved in 100 ml. of water, which also contained 14.2 g. of sodium carbonate. Vigorous agitation was maintained throughout the course of the addition, after which the reaction mixture was then further stirred at room temperature for a period of 2 hours. At this point, the precipitated solids which formed were immediately recovered by means of suction filtration, air-dried to constant weight and thereafter recrystallized from acetonitrile-methanol to give 16.6 g. (60%) of pure 4-[2-(5-bromo-2-methoxynicotinamido)-ethyl]benzenesulfonamide, m.p. 214°–215°C.

Anal. Calcd. for $C_{15}H_{16}BrN_3O_4S$: C, 43.49; H, 3.90; N, 10.15. Found: C, 43.79; H, 3.95; N, 10.08.

PREPARATION D

A 500 ml. three-necked, round-bottomed flask was charged with 14.6 g. (0.119 mole) of endo-2-aminomethylbicyclo[2.2.1]hept-5-ene [P. Wilder et al., *Journal of Organic Chemistry*, Vol. 30, p. 3078 (1965)], 18.0 g. (0.178 mole) of triethylamine and 100 ml. of tetrahydrofuran. The mixture was then rapidly cooled and stirred in an ice bath, while a solution consisting of 27.4 g. (0.119 mole) of N,N-diphenylcarbamoyl chloride dissolved in 100 ml. of tetrahydrofuran was slowly added thereto in a dropwise manner. After the addition was complete, the reaction mixture was stirred at room temperature (~25°C.) for a period of 1 hour and the resulting solution was then concentrated in vacuo (to approximately ⅓ of its original volume) to remove most of the tetrahydrofuran. On cooling, there was obtained a crystalline precipitate, which was subsequently collected by means of suction filtration and thereafter suspended in 250 ml. of 1N aqueous hydrochloric acid. Extraction of the latter aqueous solution with 3 200-ml. portions of chloroform, followed by drying of the combined organic layers then gave a clear organic solution upon filtration. After evaporating the clear filtrate to near dryness while under reduced pressure, there was ultimately obtained a heavy viscous oil, which subsequently crystallized on trituration with n-hexane. Recrystallization of the latter crystalline material from diethyl ether/n-hexane finally gave pure 1,1-diphenyl-3-(bicyclo[2.2.1]-hept-5-en-2-yl-endo-methyl)urea, m.p. 129°–130°C. The analytical sample was a crystalline white solid.

Anal. Calcd. for $C_{21}H_{22}N_2O$: C, 79.22; H, 6.96; N, 8.80. Found: C, 79.19; H, 7.05; N, 8.93.

PREPARATION E

A mixture consisting of 1.3 g. (0.01 mole) of 4-chlorocyclohexanone [prepared according to the procedure of R. Grieve et al., as described in *Chemische Berichte*, Vol. 87, p. 793 (1954)], 1.1 g. (0.016 mole) of hydroxylamine hydrochloride and 2.2 g. (0.055 mole) of sodium hydroxide in 40 ml. of ethanol and 20 ml. of water was refluxed for a period of 1 hour and then slowly concentrated in vacuo. Treatment of the resulting concentrate with 1N hydrochloric acid to pH 4.0, followed by extraction with chloroform and subsequent evaporation of the chloroform extract then gave 1.1 g. (75%) of the desired oxime [first reported by E. Miller et al., in *Chemische Berichte*, Vol. 98, p. 3501 (1965)].

A solution of 1.1 g. (0.0075 mole) of the above oxime in 50 ml. of tetrahydrofuran was then treated with 600 mg. of lithium aluminum hydride and refluxed for approximately 16 hours (overnight). On cooling to room temperature, the excess lithium aluminum hydride present in the mixture was carefully destroyed by the slow addition thereto of 20 ml. of ethyl acetate and 20 ml. of water and there was ultimately obtained, after initial conversion to the hydrochloride salt, 180 mg. (14%) of pure 4-chlorocyclohexylamine hydrochloride (m.p. 220°–221°C.) as the desired final product.

Anal. Calcd. for $C_6H_{12}ClN.HCl$: C, 42.39; H, 7.71; N, 8.24. Found: C, 42.16; H, 7.76; N, 8.33.

The procedure described in Preparation D was now followed to prepare the 1,1-diphenyl-3-(4-chlorocyclohexyl)urea compound except that 660 mg. (0.0039 mole) of 4-chlorocyclohexylamine hydrochloride in 30 ml. of tetrahydrofuran was treated with 1.95 g. (0.00195 mole) of triethylamine and the resulting mixture stirred, while 900 mg. (0.0039 mole) of N,N-diphenylcarbamoyl chloride was slowly added thereto in a dropwise manner during the course of a 10-minute period. Upon completion of this step, the reaction mixture was refluxed for a period of 2 hours and there was ultimately obtained, after the usual work-up and recrystallization step from ethyl acetate/n-hexane, 820 mg. (64%) of pure 1,1-diphenyl-3-(4-chlorocyclohexyl)urea, m.p. 116°–118°C.

Anal. Calcd. for $C_{19}H_{21}ClN_2O$: C, 69.43; H, 6.43; N, 8.52. Found: C, 69.67; H, 6.41; N, 8.47.

EXAMPLE I

To a well-stirred solution (cooled in an ice bath) consisting of 2.05 g. (0.005 mole) of 4-[2-(2-methoxynicotinamido)ethyl]-benzenesulfonamide dissolved in 30 ml. of dry N,N-dimethylformamide, there were added 750 mg. (0.006 mole) of cyclohexyl isocyanate, followed by 286 mg. (0.006 mole) of 50% sodium hydride in mineral oil. A white precipitate soon formed and vigorous hydrogen gas evolution was noted. The resulting mixture was then stirred at 60°C. for a period of approximately 17 hours, at which point thin-layer chromatography (TLC) analysis of an aliquot portion showed essentially complete conversion. After pouring the spent mixture into 150 ml. of anhydrous diethyl ether, the sodium salt of the product precipitated as a white solid and was subsequently collected by means of suction filtration. The filter cake was washed well with diethyl ether and then dissolved in 60 ml. of water. Upon acidification with 1N hydrochloric acid and extraction into chloroform, followed by decolorization with charcoal and drying over anhydrous magnesium sulfate, there was ultimately obtained a clear chloroform solution of the desired final product. Evaporation of the latter solution to near dryness while under reduced pressure then gave 1-cyclohexyl-3-{4-[2-(2-methoxynicotinamido)ethyl]benzenesulfonyl}urea as the residual material, which was subsequently twice recrystallized from acetonitrile to afford 2.12 g. (76%) of pure product, m.p. 192°–193°C.

Anal. Calcd. for $C_{22}H_{27}N_4O_5S$: C, 57.38; H, 6.13; N, 12.17. Found: C, 57.74; H, 6.18; N, 12.42.

EXAMPLE II

The procedure described in Example I was essentially followed except that 2.5 g. (0.00675 mole) of 4-[2-(5-chloro-2-methoxynicotinamido)ethyl]benzenesulfonamide and 845 mg. (0.00675 mg.) of cyclohexyl isocyanate were reacted in 25 ml. of dry N,N-dimethylformamide in the presence of 325 mg. (0.00675 mole) of 50% sodium hydride in mineral oil. In this manner, there was obtained a 1.39 g. (41.5%) yield of pure 1-cyclohexyl-3-{4-[2-(5-chloro-2-methoxynicotinamido)ethyl]benzenesulfonyl}urea, m.p. 175°–176°C.

Anal. Calcd. for $C_{33}H_{27}ClN_4O_5S$: C, 53.38; H, 5.50; N, 11.32. Found: C, 53.07; H, 5.44; N, 11.35.

EXAMPLE III

The procedure described in Example I was essentially followed except that 11.5 g. (0.0278 mole) of 4-[2-(5-bromo-2-methoxynicotinamido)ethyl]benzenesulfonamide and 3.48 g. (0.0278 mole) of cyclohexyl isocyanate were reacted in 80 m. of dry N,N-dimethylformamide in the presence of 1.18 g. (0.0278 mole) of 57% sodium hydride in mineral oil. Additionally, the reaction mixture was stirred at 65°–70°C. for only 2 hours and then allowed to stand overnight at room temperature (∼25°C.) for approximately 16 hours, while under constant agitation. In this manner, there was obtained a 7.6 g. (50%) yield of pure 1-cyclohexyl-3-{4-[2-(5-bromo-2-methoxynicotinamido)ethyl]benzenesulfonyl}urea, m.p. 183°–184°C.

Anal. Calcd. for $C_{22}H_{27}BrN_4O_5S$: C, 48.98; H, 5.05; N, 10.39. Found: 49.06; H, 5.05; N, 10.29.

EXAMPLE IV

The procedure described in Example I was essentially followed except that 1.67 g. (0.005 mole) of 4-[2-(2-methoxynicotinamido)ethyl]benzenesulfonamide and 1.59 g. (0.005 mole) of 1,1-diphenyl-3-(bicyclo[2.2.1]hept-5-en-2-yl-endo-methyl)urea were reacted in 25 ml. of dry N,N-dimethylformamide in the presence of 240 mg. (0.005 mole) of 50% sodium hydride in mineral oil. Additionally, the reaction mixture was heated with stirring at 70°C. for a period of only 4 hours and column chromatography (using $SiO_2$/95% $CHCl_3$/2.5% $CH_3OH$/2.5% $CH_3COOH$) was necessary during the final purification stage. In this manner, there was ultimately obtained a 120 mg. (5%) yield of pure 1-(bicyclo[2.2.1]hept-5-en-2-yl-endo-methyl)-3-{4-[2-(2-methoxynicotinamido)ethyl]benzenesulfonyl}urea, m.p. 164°–165°C.

Anal. Calcd. for $C_{24}H_{28}N_4O_5S$: C, 59.49; H, 5.83; N, 11.58. Found: C, 59.59; H, 5.86; N, 11.56.

EXAMPLE V

The procedure described in Example I was essentially followed except that 1.48 g. (0.004 mole) of 4-[2-(5-chloro-2-methoxynicotinamido)ethyl]benzenesulfonamide and 1.27 g. (0.004 mole) of 1,1-diphenyl-3-(bicyclo[2.2.1]hept-5-en-2-yl-endo-methyl)urea were reacted in 50 ml. of dry N,N-dimethylformamide in the presence of 192 mg. (0.004 mole) of 50% sodium hydride in mineral oil. Additionally, it was necessary to employ column chromatography (using $SiO_2$/95%$CHCl_3$/2.5%$CH_3OH$/2.5%$CH_3COOH$) during the final purification stage. In this manner, there was ultimately obtained a 328 mg. (16%) yield of 1-(bicyclo[2.2.1]-hept-5-en-2-yl-endo-methyl)-3-{4-[2-(5-chloro-2-metoxynicotinamido)ethyl]benzenesulfonyl}urea, m.p. 158°–160°C. (dec.) after recrystallization from acetonitrile/diethyl ether.

Anal. Calcd. for $C_{24}H_{27}ClN_4O_5S$: C, 55.54; H, 5.24; N, 10.80. Found: C, 55.20; H, 5.36; N, 10.53.

EXAMPLE VI

The procedure described in Example I was essentially followed except that 2.07 g. (0.005 mole) of 4-[2-(5-bromo-2-methoxynicotinamido)ethyl]benzenesulfonamide and 1.59 g. (0.005 mole) of 1,1-diphenyl-3-(bicyclo[2.2.1]hept-5-en-2-yl-endo-methyl)urea were reacted in 30 ml. of dry N,N-dimethylformamide in the presence of 240 mg. (0.005 mole) of 50% sodium hydride in mineral oil. Additionally, the reaction mixture was stirred at 65°C. for a period of only 6 hours and then allowed to stand overnight at room temperature for approximately 16 hours while under constant agitation. It was also necessary to employ column chromatography (using $SiO_2$/95% $CHCl_3$/2.5% $CH_3OH$/2.5% $CH_3COOH$) during the final purification step. In this manner, there was ultimately obtained a 590 mg. (21%) yield of 1-(bicyclo[2.2.1]hept-5-en-2-yl-endo-methyl)-3-{4-[2-(5-bromo-2-methoxynicotinamido)ethyl]benzenesulfonyl}urea, m.p. 158°–160°C. (dec.) after recrystallization from acetonitrile/n-hexane (1:5 by volume).

Anal. Calcd. for $C_{24}H_{27}BrN_4O_5S$: C, 51.15; H, 4.83; N, 9.94. Found: C, 51.14; H, 4.86; N, 9.79.

EXAMPLE VII

The procedure described in Example I was essentially followed except that 555 mg. (0.0015 mole) of 4-[2-(5-chloro-2-methoxynicotinamido)ethyl]benzenesulfonamide and 495 mg. (0.0015 mole) of 1,1-diphenyl-3-(4-chlorocyclohexyl)urea were reacted in 10 ml. of dry N,N-dimethylformamide in the presence of 72 mg. (0.0015 mole) of 50% sodium hydride in mineral oil. Additionally, the reaction mixture was only stirred at room temperature (without heating) for a period of approximately 24 hours. In this manner, there was obtained an 88 mg. (11%) yield of pure 1-(4-chlorocyclohexyl)-3-{4-[2-(5-chloro-2-methoxynicotinamido)ethyl]benzenesulfonyl}urea, m.p. 165°–167°C. after recrystallization from acetonitrile/diethyl ether.

Anal. Calcd. for $C_{22}H_{26}Cl_2N_4O_5S$: C, 49.90; H, 4.95; N,10.58. Found: C, 49.81; H, 4.90; N, 10.48.

EXAMPLE VIII

The procedure described in Example VII is repeated except that 4-[2-(2-methoxynicotinamido)ethyl]benzenesulfonamide is the starting material of choice employed in lieu of the 5-chloro derivative, again on the same molar basis as before. In this particular case, the corresponding final product thus obtained is 1-(4-chlorocyclohexyl)-3-{4-[2-(2-methoxynicotinamido)ethyl]-benzenesulfonyl}urea.

In like manner, the use of 4-[2-(5-bromo-2-methoxynicotinamido)ethyl]benzenesulfonamide as starting material in place of the corresponding 5-chloro compound in the same reaction procedure described above affords 1-(4-chlorocyclohexyl)-3-{4-[2-(5-bromo-2-methoxynicotinamido)ethyl]benzenesulfonyl}urea as the desired final product which is obtained.

EXAMPLE IX

The sodium salt of 1-cyclohexyl-3-{4-[2-(5-bromo-2-methoxynicotinamido)ethyl]benzenesulfonyl}urea was prepared by dissolving 4.5 g. of said compound in 30 ml. of anhydrous ethanol (i.e., absolute alcohol) and then adding to said alcoholic solution an equivalent amount of moles of sodium methoxide (viz., 450 mg. of $NaOCH_3$). Upon removal of the resulting precipitate by means of filtration and its subsequent recrystallization from an ethanol-methanol mixture, there was obtained a 3.05 g. yield of the desired alkali metal salt in the form of a white crystalline solid (m.p. 250°–252°C.) which is freely-soluble in water.

In like manner, the potassium and lithium salts are also similarly prepared, as are the alkali metal salts of the other benzenesulfonylureas of this invention which are reported in the previous examples.

EXAMPLE X

The calcium salt of 1-(bicyclo[2.2.1]hept-5-en-2-yl-endomethyl)-3-{4-[2-(2-methoxynicotinamido)ethyl]-benzenesulfonyl}-urea is prepared by dissolving said compound in water containing an equivalent amount of in moles of calcium hydroxide and then freeze-drying the mixture. The corresponding magnesium salt is also prepared in like manner, as are all the other alkaline-earth metal salts not only of this particular compound, but also of those acidic benzenesulfonylureas previously described in Examples I–III and V–VIII, respectively.

EXAMPLE XI

A dry solid pharmaceutical composition is prepared by blending the following materials together in the proportions by weight specified below:

| | |
|---|---|
| 1-Cyclohexyl-3-{4-[2-(5-bromo-2-methoxynicotinamido)ethyl]benzenesulfonyl}urea | 50 |
| Sodium citrate | 25 |
| Alginic acid | 10 |
| Polyvinylpyrrolidone | 10 |
| Magnesium stearate | 5 |

After the dried composition is thoroughly blended, tablets are punched from the resulting mixture, each tablet being of such size that it contains 50 mg. of the active ingredient. Other tablets are also prepared in a similar fashion containing 2.5, 5, 10, and 25 mg. of the active ingredient, respectively, by merely using the appropriate amount of the benzenesulfonyl-urea in each case.

EXAMPLE XII

A dry solid pharmaceutical composition is prepared by combining the following materials together in the proportions by weight indicated below:

| | |
|---|---|
| 1-(bicyclo[2.2.1]hept-5-en-2-yl-endo-methyl)-3-{4-[2-(2-methoxynicotinamido)ethyl]-benzenesulfonyl}urea | 50 |
| Calcium carbonate | 20 |
| Polyethylene glycol, average molecular weight, 4000 | 30 |

The dried solid mixture so prepared is then thoroughly agitated so as to obtain a powdered product that is completely uniform in every respect. Soft elastic and hard-filled gelatin capsules containing this pharmaceutical composition are then prepared, employing a sufficient quantity of material in each instance so as to provide each capsule with 75 mg. of the active ingredient.

EXAMPLE XIII

The benzenesulfonyl urea final products of Example I–VII were tested for hypoglycemic activity in groups of 6 male albino rats (each weighing approximately 190–240 g.) of the Sprague-Dawley strain. No anesthetic was used in this study. The rats were fasted for approximately 18–24 hours prior to administration, a blood sample was then taken from the tail vein of each animal and the test compound was administered intraperitoneally (while in solution as the sodium salt in 0.9% saline) at dose levels of 1.0, 0.5 and 0.1 mg/kg., respectively. Additional blood samples were then take at 1, 2 and 4 hour intervals after administration of the drug. The samples were immediately diluted 1:10 (by volume) with 1.0% heparin in 0.9% saline. Blood glucose was determined by adapting the method of W. S. Hoffman [see *Journal of Biological Chemistry*, Vol. 120, p.51 (1937)]to the Autoanalyzer instrument produced by Technicon Instruments Corporation of Chauncey, N.Y. On this basis, the maximum percent decrease in blood sugar was calculated and reported as such (i.e., as hypoglycemic activity for the various compounds listed in the table below:

| Sulfonylurea | Hypoglycemic Activity (Max.%Fall) | | |
|---|---|---|---|
| | 0.1mg./kg. | 0.5mg./kg. | 1.0mg./kg. |
| Prod. of Ex. I | 17 | 34 | 48 |
| Prod. of Ex. II | 26 | 47 | 49 |
| Prod. of Ex. III | 27 | 42 | 48 |
| Prod. of Ex. IV | 36 | 51 | 46 |
| Prod. of Ex. V | 30 | 46 | 44 |
| Prod. of Ex. VI | — | 32 | 42 |
| Prod. of Ex. VII | 22 | 37 | 50 |

What is claimed is:

1. A method for lowering blood sugar in the treatment of a diabetic animal, which comprises orally administering to said animal an effective blood sugar lowering amount of a compound selected from the group consisting of benzenesulfonylureas of the formula:

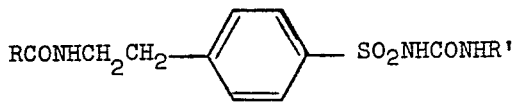

and the base salts thereof with pharmacologically acceptable cations, wherein R is 2-methoxy-3-pyridyl, 5-chloro-2-methoxy-3-pyridyl or 5-bromo-2-methoxy-3-pyridyl, and R′ is bicyclo-[2.2.1]hept-5-en-2-yl-endo-methyl, cyclohexyl or 4-chlorocyclohexyl.

2. The method as claimed in claim 1 wherein the compound administered is 1-(bicyclo[2.2.1]hept-5-en-2-yl-endo-methyl-3-{4-[2-(2-methoxynicotinamido)ethyl]benzenesulfonyl}urea.

3. The method as claimed in claim 1 wherein the compound administered is 1-cyclcohexyl-3-{4-[2-(2-methoxynicotinamido)ethyl]-benzenesulfonyl}urea.

4. The method as claimed in claim 1 wherein the compound administered is 1-(bicyclo[2.2.1]hept-5-en-2-yl-endo-methyl)-3-{4-[2-(5-chloro-2-methoxynicotinamido)ethyl]benzenesulfonyl}urea.

5. The method as claimed in claim 1 wherein the compound administered is 1-cyclohexyl-3-{4-[2-(5-chloro-2-methoxynicotinamido)-ethyl]benzenesul-}fonyl urea.

6. The method as claimed in claim 1 wherein the compound administered is 1-(4-chlorocyclohexyl)-3-{4-[2-(5-chloro-2-methoxynicotinamido)ethyl]benzenesulfonyl}urea.

7. The method as claimed in claim 1 wherein the compound administered is 1-(bicyclo[2.2.1]hept-5-en-2-yl-endo-methyl)-3-{4-[2-(5-bromo-2-methoxynicotinamido)ethyl]benzenesulfonyl}urea.

8. The method as claimed in claim 1 wherein the compound administered is 1-cyclohexyl-3-{4-[2-(5-bromo-2-methoxy-nicotinamido)-ethyl]benzenesulfonyl}urea.

9. A composition suitable for oral administration comprising a pharmaceutically acceptable carrier and an effective blood sugar lowering amount of an oral hypoglycemic agent selected from the group consisting of benzenesulfonylureas of the formula:

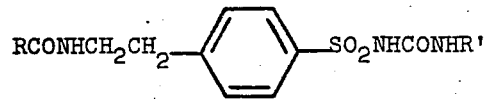

and the base salts thereof with pharmacologically acceptable cations, wherein R is 2-methoxy-3-pyridyl, 5-chloro-2-methoxy-3-pyridyl or 5-bromo-2-methoxy-3-pyridyl, and R′ is bicyclo-[2.2.1]hept-5-en-2-yl-endo-methyl, cyclohexyl or 4-chlorocyclohexyl.

10. The composition according to claim 9 wherein the hypoglycemic agent is 1-cyclohexyl-3-{4-[2-(5-chloro-2-methoxynicotinamido)ethyl]benzenesulfonyl}urea.

11. The composition according to claim 9 wherein the hypoglycemic agent is 1-cyclohexyl-3-{4-[2-(5-bromo-2-methoxynicotinamido)ethyl]benzenesulfonyl}urea.

12. The composition according to claim 9 wherein the hypoglycemic agent is 1-(bicyclo[2.2.1]hept-5-en-2-yl-endomethyl)-3-{4-[2-(2-methoxynicotinamido)ethyl]benzenesulfonyl}urea.

13. The composition according to claim 9 wherein the hypoglycemic agent is 1-(bicyclo[2.2.1]hept-5-en-2-yl-endo-methyl)-3-{4-[2-(5-chloro-2-methoxynicotinamido)ethyl]benzenesulfonyl}urea.

14. The composition according to claim 9 wherein the hypoglycemic agent is 1-(4-chlorocyclohexyl)-3-{4-[2-(5-chloro-2-methoxynicotinamido)ethyl]benzenesulfonyl}urea.

* * * * *